United States Patent [19]

Kvamme

[11] Patent Number: 5,520,948
[45] Date of Patent: May 28, 1996

[54] HIGH ACID SYSTEM NUTRITIONAL FORMULATIONS

[75] Inventor: Candis D. Kvamme, Brooklyn Park, Minn.

[73] Assignee: Sandoz Ltd., Basel, Switzerland

[21] Appl. No.: 395,346

[22] Filed: Feb. 28, 1995

Related U.S. Application Data

[63] Continuation of Ser. No. 809,852, Dec. 18, 1991, abandoned, which is a continuation of Ser. No. 608,072, Nov. 1, 1990, abandoned.

[51] Int. Cl.$^6$ .......................................................... A23L 2/00
[52] U.S. Cl. ........................... 426/590; 426/599; 426/72; 426/73; 426/74; 426/262; 426/330.3; 426/330.5
[58] Field of Search .................................. 426/599, 590, 426/72–74, 262, 330.3, 330.5

[56] References Cited

U.S. PATENT DOCUMENTS

| | | |
|---|---|---|
| 2,919,195 | 12/1959 | Block . |
| 3,876,806 | 4/1975 | Hempenius et al. . |
| 3,897,570 | 7/1975 | Yokotsuka et al. . |
| 4,100,024 | 7/1978 | Adler-Nissen . |
| 4,251,550 | 2/1981 | Proctor . |
| 4,414,238 | 11/1983 | Schmidl . |
| 4,478,855 | 10/1984 | Dahlen et al. . |
| 4,486,413 | 12/1984 | Wiesenberger et al. . |
| 4,497,800 | 2/1985 | Larson et al. . |
| 4,670,268 | 6/1987 | Mahmoud . |
| 4,834,990 | 5/1989 | Amer . |
| 4,871,550 | 10/1989 | Millman . |
| 4,988,530 | 1/1991 | Hoersten et al. . |
| 5,021,245 | 6/1991 | Borschel et al. . |

FOREIGN PATENT DOCUMENTS

| | | |
|---|---|---|
| 25803 | 12/1978 | Australia . |
| 532506 | 6/1980 | Australia . |
| 5734280 | 10/1980 | Australia . |
| 0246747 | 11/1987 | European Pat. Off. . |
| 0265772 | 5/1988 | European Pat. Off. . |
| 0371659 | 6/1990 | European Pat. Off. . |
| 2623394 | 5/1989 | France . |
| 9109538 | 7/1991 | WIPO . |

OTHER PUBLICATIONS

Milk Proteins:Physicochemical & Functional Properties, Kinsella, et al., CRC, vol. 21, Issue 3, pp. 197–262.
Proteins in Whey:Chem., Physical & Functional Properties; Advances in Food & Nutrition Research, vol. 33, Kinsella, et al., pp. 343–439.

The Taste of Commercially Available Supplemental Elemental Diets; Seltzer, et al., pp. 471–472.

Parenteral & Enteral Food Systems; Food Technology—Jul. 1988; Schmidl, et al., pp. 77–85.

Elemental Diets in Management of Clinical Nutritional Problems; Modern Medicine of Canada; May 1974, vol. 29, No. 5, Deitel, et al.

Elemental Diets—Facts and Fantasies; Gastroenterology '80, Koretz and Meyer, vol. 78, pp. 393–410.

Enteral Alimentation—An Update on New Products, Nutritional Support Services, vol. 1, No. 8, Dec. 1981, McIntire, et al. pp. 7–14.

Progress Report:Elemental Diets, Gut, 1975, R. I. Russell, pp. 68–77.

Nitrogen Sources in Enteral Feeding, (in review for publication), Schmidl, et al., pp. 2–19.

Whey Proteins & Their Thermal Denaturation—A Review, Irish Journal of Food Science & Technology, '87, Mulvihill, et al., pp. 43–75.

Functionality of Heated Milk Proteins in Dairy & Related Foods, Journal of Dairy Science, vol. 68, No. 10, '85; Morr, et al., pp. 2772–2781.

Thermal Denaturation and Aggregation of Whey Proteins, Donovan and D. M. Mulvihill, Irish Journal '87, pp. 87–100.

Symposium:Assessing Functionality of Whey Proteins, Journal of Dairy Science, vol. 67, No. 11, '84, Nicholas Melachouris.

*Primary Examiner*—Carolyn Paden
*Attorney, Agent, or Firm*—Robert S. Honor; Carl W. Battle

[57] ABSTRACT

Improved nutritional formulations based on the total formulation calories, of about 40 to 90% of calories as carbohydrates, about 2 to 30% of calories as protein, about 0 to 35% of calories as fat, and about 0 to 17% of calories as fiber. The formulations may also contain 100% of U.S. RDA of vitamins and minerals. The formulations have a high acid (low pH) content (e.g., pH 3.5–3.9). The formulations may be carbonated or non-carbonated. The formulations are preferably used as an oral nutritional supplement providing about 1.0 calorie/ml.

17 Claims, No Drawings

HIGH ACID SYSTEM NUTRITIONAL FORMULATIONS

This is a continuation of application Ser. No. 07/809,852, filed Dec. 18, 1991, now abandoned, which in turn is a continuation of application Ser. No. 07/608,072, filed Nov. 1, 1990, now abandoned.

This invention relates to improved liquid nutritional formulations. More particularly, it relates to improved liquid oral nutritional supplement formulations.

FIELD OF THE INVENTION

There are numerous oral nutritional supplements on the market. However, currently all are low acid (high pH) dairy based products; typically vanilla, chocolate or strawberry flavored at present. There are no ready-to-drink nutrition supplements providing alternatives to these "milky tasting products". The present invention provides liquid oral nutritional formulations which have a juice-like consistency and flavor.

SUMMARY OF THE INVENTION

The present invention provides improved liquid oral nutritional formulations. The improved formulations are comprised based on the total formulation calories of about 40 to 90% of calories as carbohydrates, about 2 to 30% of calories as protein, about 0 to 35% of calories as fat, and about 0 to 17% of calories as fiber. The formulations may also contain 100% of U.S. RDA of vitamins and minerals. The formulations have a high acid (low pH) content (e.g., pH3.5–3.9). The formulations may be carbonated or non-carbonated. The present formulations are preferably used as an oral nutritional supplement providing about 1.0 calorie/ml.

DETAILED DESCRIPTION OF THE INVENTION

The carbohydrate source may be sucrose, corn syrup solids, glucose, fructose, maltodextrin or combinations thereof. Sucrose is preferred. When using corn syrup solids or maltodextrin, it is preferred that they be used in combination with either sucrose, glucose or fructose, or combinations of sucrose, glucose or fructose with the corn syrup solids or maltodextrin content of the combination being less than about 40% of the total combination. Also, combinations of corn syrup solids and maltodextrin may be used with either sucrose, glucose, fructose, or combinations of sucrose, glucose or fructose provided that the combination of corn syrup solids and maltodextrin is less than about 40% of the total combination. Concentrations of corn syrup solids, maltodextrin or combinations thereof, are maintained below 40% of the total carbohydrate source to minimize Maillard browning.

Artificial sweeteners e.g., saccharin and aspartame, may also be used to enhance the organoleptic quality of the formulations.

The amount of carbohydrate may preferably be from about 60% to 85% of total formulation calories.

The protein source may be whey protein concentrate (whey), caseinate, soy protein, egg whites or combinations thereof. Whey is preferred because of its good flavor, and solubility at low pH. Caseinate, soy protein and egg white may used in combination with the whey, at a concentration of at least 60% whey. At concentrations above 40%, caseinate and soy protein tend to precipitate and impart a poor taste to the formulations, whereas egg whites at concentrations above 40% tend to gel at processing temperatures.

The amount of protein may be preferably from about 5–25% of total formulation calories.

The fat source of the formulations may be any fat source or blend of fat sources which provide the desired amount of fat calories. Preferably the fat source should be high in monounsaturated fatty acids. Fat sources may include vegetable oils, e.g., high oleic acid vegetable oils such as sunflower oil, canola oil, and olive oil; safflower oil, cottonseed oil, corn oil or soybean oil, and medium chain triglycerides e.g., C6–C12 triglycerides. High oleic acid sunflower oil is preferred.

Marine oils and butter fat may also be used.

The fat source may preferably be from about 0 to 25% of the total formulation calories.

The fiber source may be guar gum, pectin, soy polysaccharide, gum arabic and the like or combinations thereof. Guar gum and pectin are preferred. The fiber may preferably be from about 0–5% of the total formulation calories.

It has been found that during heat processing and storage time a high ion concentration, especially sodium ion and potassium ion, causes gellation of the protein of the formulations. To overcome this problem, the potassium content of the formulations is limited to about 0 to 10 mg per 100 ml (0 to 23.7 mg per 8 oz); and the sodium content of the formulations is limited to about 0 to 30 mg per 100 ml (0 to 71.1 per 8 oz). It will be understood that the sodium and potassium ions are supplied naturally (without added salts) by adjusting the combination of carbohydrates and protein.

The presence of reducing sugars and protein (which contain alpha amino acid groups) makes the formulations susceptible to nonenzymatic browning, which causes an undesirable color and unpleasant flavor. This browning effect may be reduced by maintaining the formulations at a low pH of 3.5–3.9. Further reduction in nonenzymatic browning without pH change may be achieved by the addition of cysteine, which inhibits this reaction, or by the use of sucrose, a non reducing sugar, or a combination of both.

Acids such as phosphoric acid, citric acid, malic acid, tartaric acid, fumaric acid, adipic acid, lactic acid, or combinations thereof, may be used for pH control. However, the combination of phosphoric acid and citric acid is preferred. A ratio of citric acid to phosphoric acid of 1 to 1.9 preferably 0.77 to 1.0 may be so used for pH control.

To inhibit nonenzymatic browning, cysteine may be added in free form from about 0.025 to 0.20% on a weight/weight (w/w) basis, based on the total weight of the liquid formulation. The preferred amount is from about 0.04% to 0.1% (w/w).

Free amino acids may be added to the present formulations for nutritional benefits. Supplementation with free amino acids normally imparts a detrimental flavor to nutritional products. However, amino acids such as arginine, cysteine, isoleucine, leucine, valine or combinations thereof may be added to the present formulations without negative flavor impact due to the present low pH system.

The amino acids are preferably added from about 0 to 1.0% (w/w) basis, based on the total weight of the liquid formulation.

The following Tables I, II and III illustrate preferred nutritional formulations.

Table I shows the nutritional profile of formulations with and without fat. Table II lists the actual ingredients of .the nutritional profile of Table I without fat. Table III lists the actual ingredients of the nutritional profile of Table I with fat.

TABLE I

NUTRITIONAL PROFILE
LIQUID NUTRITIONAL FORMULATION

|  |  | WITH FAT PER 237 ml | WITHOUT FAT PER 237 ml |
|---|---|---|---|
| PROTEIN | 8.8 g |  |  |
| CARBOHYDRATE |  g | 39.2 | 36.0 |
| FAT |  g | 5.3 | 0.0 |
| ENERGY | kcal | 240 | 180 |
| VITAMIN A | 625 IU |  |  |
| VITAMIN D | 50 IU |  |  |
| VITAMIN E | 5.7 IU |  |  |
| VITAMIN C | 37.5 mg |  |  |
| FOLIC ACID | 50 mcg |  |  |
| THIAMINE | 0.38 mg |  |  |
| RIBOFLAVIN | 0.43 mg |  |  |
| NIACIN | 5.0 mg |  |  |
| PYRIDOXINE ($B_6$) | 0.5 mg |  |  |
| CYANOCOBALAMIN ($B_{12}$) | 1.5 mcg |  |  |
| BIOTIN | 37.5 mcg |  |  |
| PANTOTHENIC ACID | 1.25 mg |  |  |
| CALCIUM | 135 mg |  |  |
| PHOSPHORUS | 160 mg |  |  |
| IODINE | 18.8 mcg |  |  |
| IRON | 2.25 mg |  |  |
| MAGNESIUM | 50 mg |  |  |
| COPPER | 0.25 mg |  |  |
| ZINC | 3.75 mg |  |  |
| VITAMIN K | 9.0 mcg |  |  |
| CHOLINE | 130 mg |  |  |
| POTASSIUM | 10 mg |  |  |
| SODIUM | 35 mg |  |  |
| CHLORIDE | 220 mg |  |  |
| MANGANESE | 0.5 mg |  |  |

CALORIC DISTRIBUTION

|  | | |
|---|---|---|
| PROTEIN | 15% | 20% |
| CARBOHYDRATE | 65% | 80% |
| FAT | 20% | 0% |
| kcal/ml | 1.0 | 0.76 |

TABLE II

ACTUAL INGREDIENTS
LIQUID NUTRITIONAL FORMULATION
WITHOUT FAT

| Ingredients | GRAMS/237 ml | % Formula |
|---|---|---|
| Deionized Water | 203.2 | 80.4 |
| Sucrose | 35.64 | 14.1 |
| Whey Protein Concentrate | 9.81 | 3.88 |
| Magnesium Gluconate | 1.01 | 0.400 |
| Phosphoric Acid (75%) | 0.784 | 0.310 |
| Citric Acid | 0.455 | 0.180 |
| Calcium Chloride | 0.480 | 0.190 |
| Corn Syrup Solids | 0.526 | 0.208 |
| Choline Bitartrate | 0.306 | 0.121 |
| Flavor/Color orange/yellow No. 6 | 0.265 | 0.105 |
| Ascorbic Acid | 0.095 | 0.038 |
| Cysteine | 0.1264 | 0.050 |
| Vitamin E Acetate | 0.0296 | 0.0117 |
| Zinc Sulfate | 0.01360 | 0.00538 |
| Ferrous Sulfate | 0.00841 | 0.00333 |
| Niacinamide | 0.00654 | 0.00259 |
| Vitamin A Palmitate | 0.00500 | 0.00198 |

TABLE II-continued

ACTUAL INGREDIENTS
LIQUID NUTRITIONAL FORMULATION
WITHOUT FAT

| Ingredients | GRAMS/237 ml | % Formula |
|---|---|---|
| d-Calcium Pantothenate | 0.003020 | 0.001195 |
| Cyanocobalamin | 0.002480 | 0.000981 |
| Copper Gluconate | 0.002230 | 0.000882 |
| Manganese Sulfate | 0.002120 | 0.000840 |
| Vitamin $K_1$ | 0.001650 | 0.000653 |
| Thiamine Hydrochloride | 0.000885 | 0.000350 |
| Pyridoxine Hydrochloride | 0.000880 | 0.000348 |
| Vitamin $D_3$ | 0.000800 | 0.000320 |
| Riboflavin | 0.000556 | 0.000220 |
| Folic Acid | 0.000074 | 0.000029 |
| Biotin | 0.000058 | 0.000023 |
| Potassium Iodide | 0.000032 | 0.000013 |
|  | 252.8 gm | 100.% |

TABLE III

ACTUAL INGREDIENTS
LIQUID NUTRITIONAL FORMULATIONS
WITH FAT AND FIBER

| Ingredients | Grams/237 ml Serving | % Formula |
|---|---|---|
| Deionized Water | 195.1 | 77.2 |
| Sucrose | 37.7 | 14.9 |
| Whey Protein Concentrate | 9.81 | 3.88 |
| Sunflower oil | 5.3 | 2.1 |
| Magnesium Gluconate | 1.01 | 0.400 |
| Hydrolized guar gum | 0.632 | 0.250 |
| Phosphoric Acid (75%) | 0.784 | 0.310 |
| Citric Acid | 0.455 | 0.180 |
| Emulsifier-polyglycerol ester | 0.1264 | 0.050 |
| Calcium Chloride | 0.480 | 0.190 |
| Corn Syrup Solids | 0.526 | 0.208 |
| Choline Bitartrate | 0.306 | 0.121 |
| Flavor/Color orange/yellow No. 6 | 0.265 | 0.105 |
| Ascorbic Acid | 0.095 | 0.038 |
| Cysteine | 0.1264 | 0.050 |
| Vitamin E Acetate | 0.0296 | 0.0117 |
| Zinc Sulfate | 0.01360 | 0.00538 |
| Ferrous Sulfate | 0.00841 | 0.00333 |
| Niacinamide | 0.00654 | 0.00259 |
| Vitamin A Palmitate | 0.00500 | 0.00198 |
| d-Calcium Pantothenate | 0.003020 | 0.001195 |
| Cyanocobalamin | 0.002480 | 0.000981 |
| Copper Gluconate | 0.002230 | 0.000882 |
| Manganese Sulfate | 0.002120 | 0.000840 |
| Vitamin $K_1$ | 0.001650 | 0.000653 |
| Thiamin Hydrochloride | 0.000885 | 0.000350 |
| Pyridoxine Hydrochloride | 0.000880 | 0.000348 |
| Vitamin $D_3$ | 0.000800 | 0.000320 |
| Riboflavin | 0.000556 | 0.000220 |
| Folic Acid | 0.000074 | 0.000029 |
| Biotin | 0.000058 | 0.000023 |
| Potassium Iodide | 0.000032 | 0.000013 |
|  | 252.8 gm | 100.0% |

EXAMPLE 1

Liquid Nutritional Formulation without Fat (8,000 lbs)

310.4 lbs. of whey protein concentrate, and 1,128.0 lbs. of sucrose are added to 5,932.0 lbs. of deionized water in a 1000 gallon processing vessel. A solution of 24.8 lbs. of phosphoric acid and 14.4 lbs. of citric acid in 500 lbs. of deionized water are slowly added with agitation to the mixture in the processing vessel.

78.0 lbs. of a vitamin/mineral premix, and 4.0 lbs. of cysteine are, then added with agitation to the processing vessel, and allowed to mix thoroughly.

The formulation (70°–80° F.) from the processing vessel is pumped through a two-stage Gaulin homogenizer. The second stage pressure is 500 PSI, and the first stage pressure is 2500 PSI. The product flows from the homogenizer to a plate heat exchanger where it is cooled to 40° F. and then pumped to a 2nd 1000 gallon processing vessel. 8.4 lbs. of flavor and color orange/yellow No. 6 are added slowly with agitation to the 2nd vessel.

After 10 minutes of mixing, quality control samples are taken for moisture (80.0%), pH (pH 3.8), specific gravity (1.067) and vitamin content (48 mgC/100 gms of solution).

The product is sterilized in a Cherry Burrell Unitherm thermo-processor at a minimum processing temperature of 204° F., for 4.33 seconds residence in the hold tube.

The product is then cooled to 160° F. and aseptically homogenized in a two-stage homogenizer (pressure settings as above), and aseptically packaged (at 70° F.) in 8 oz. (237 ml) Tetra Brik packages.

EXAMPLE 2

Liquid Nutritional Formulation with Fat and Fiber (8,000 lbs.)

An emulsifier solution of 4 lb. of polyglycerol ester in 100.0 lbs. of (180° F.) deionized water is added to 5326.0 lbs. of deionized water in a 1,000 gallon processing vessel. 20 lbs. of hydrolyzed guar gum, 310.4 lbs. of whey protein concentrate, and 1192.0 lbs. of sucrose are added to the processing vessel and mixed with the emulsifier solution. 168.0 lbs. of high oleic sunflower oil is then added to the processing vessel and the ingredients mixed thoroughly. A solution of 24.8 lbs. of phosphoric acid and 14.4 lbs. of citric acid in 500 lbs. of deionized water are slowly added with agitation to the mixture in the processing vessel. The mixture is then heated to 160°–165° F.

62.0 lbs. of a mineral premix, and 4.0 lbs. of cysteine are then added with agitation to the processing vessel, and allowed to mix thoroughly.

The formulation (160°–165° F.) from the processing vessel is pumped twice through a two-stage Gaulin homogenizer. The second stage pressure is 500 PSI, and the first stage pressure is 2500 PSI. The product flows from the homogenizer to a plate heat exchanger where it is cooled to 40° F. The mixture is then pumped to a 2nd 1,000 gallon processing vessel. 16.0 lbs. of vitamin premix in 250 lbs. of deionized water are added to the processing vessel. 8.4 lbs. of flavor and color orange/yellow No. 6 are then added slowly with agitation to the 2nd vessel.

After 10 minutes of mixing, quality control samples are taken for moisture (78.0%), pH (pH 3.8), specific gravity (1.067) and vitamin C content (48 mgC/100 gms of solution).

The product is sterilized in a Cherry Burrell Unitherm thermo-processor at a minimum processing temperature of 204° F., for 4.33 seconds residence in the hold tube.

The product is then cooled to 160° F. and aseptically homogenized in a two-stage homogenizer (pressure settings as above), and aseptically packaged (at 70° F.) in 8 oz. (237 ml) Tetra Brik packages.

What is claimed is:

1. Liquid oral nutritional formulation comprising based on the total formulation calories about 40 to 90% of calories as carbohydrates, about 2 to 30% of calories as protein, about 0 to 35% of calories as fat, and about 0 to 17% of calories as fiber; characterized in that the formulation contains a combination of sucrose and L-cysteine to reduce non-enzymatic browning and has a pH of from about 3.5 to 3.9; wherein said L-cysteine comprises from about 0.025 to about 0.20% based on total weight of said formulation, and said sucrose comprises about 40 to 90% of the total formulation calorie, and said protein comprises at least 60% by weight whey protein.

2. The oral nutritional formulations of claim 1 having in addition 100% of U.S. RDA of vitamins and minerals.

3. The oral nutritional formulations of claim 2 comprising one or more amino acids selected from the group consisting of arginine, isoleucine, leucine, valine and combinations thereof.

4. The oral nutritional formulations of claim 1, wherein the carbohydrates comprise from about 60 to 85% of the total formulation calories.

5. The oral nutritional formulations of claim 1, wherein protein comprises from about 5 to 25% of the total formulation calories.

6. The oral nutritional formulations of claim 1, wherein the fat comprises from about 0 to 25% of the total formulation calories.

7. The oral nutritional formulations of claim 1, wherein the fiber comprises from about 0 to 5% of the total formulation calories.

8. The oral nutritional formulations of claim 1 wherein the carbohydrate source is selected from the group consisting of corn syrup solids, glucose, fructose, maltodextrin, and combinations thereof.

9. The oral nutritional formulations of claim 8 provided that when corn syrup solids or maltodextrin is used, that the corn syrup solids or maltodextrin be used in combination with either, glucose, or fructose, or combinations of, glucose or fructose, with the corn syrup solids or maltodextrin content of the combination being less than 40% of the total carbohydrate combination.

10. The oral nutritional formulations of claim 8 provided that when a combination of corn syrup solids and maltodextrin is used, that the corn syrup solids and maltodextrin be used in combination with either, glucose, or fructose, or combinations of, glucose or fructose, with the corn syrup solids and maltodextrin content of the combination being less than 40% of the total carbohydrate combination.

11. The oral nutritional formulations of claim 1 wherein the protein source is selected from the group consisting of whey protein, caseinate, soy protein, egg whites and combinations thereof.

12. The oral nutritional formulations of claim 1 wherein the fat source is selected from the group consisting of high oleic acid sunflower oil, canola oil, olive oil; safflower oil, cottonseed oil, corn oil, soybean oil and medium chain triglycerides.

13. The oral nutritional formulations of claim 1 wherein the fiber source is selected from the group consisting of guar gum, pectin, soy polysaccharide, gum arabic and combinations thereof.

14. The oral nutritional formulations of claim 1 wherein the potassium content of the formulations is from about 0 to 10 mg per 100 ml of formulation, and the sodium content of the formulations is from about 0 to 30 mg per 100 ml of formulation.

15. The oral nutritional formulations of claim 14 wherein the potassium and sodium content is provided by the carbohydrate source or the protein source.

16. The oral nutritional formulations of claim 1 wherein the pH is controlled by acids selected from the group consisting of phosphoric acid, citric acid, tartaric acid, fumaric acid, adipic acid, lactic acid, and combinations thereof.

17. The oral nutritional formulations of claim 16 wherein the acids are a combination of phosphoric acid and citric acid.

* * * * *